US010482314B2

(12) United States Patent
Syvertsen et al.

(10) Patent No.: US 10,482,314 B2
(45) Date of Patent: Nov. 19, 2019

(54) AUTOMATIC CALCULATION FOR PLOIDY CLASSIFICATION

(71) Applicant: Oslo Universitetssykehus, Institute for Cancer Genetics and Informatics, Oslo (NO)

(72) Inventors: Rolf Anders Syvertsen, Oslo (NO); Tarjei Sveinsgjerd Hveem, Oslo (NO); John Robert Maddison, Crowborough (GB); Havard Emil Greger Danielsen, Oslo (NO)

(73) Assignee: OSLO UNIVERSITETSSYKEHUS, INSTITUTE FOR CANCER GENETICS AND INFORMATICS, Oslo (NO)

( * ) Notice: Subject to any disclaimer, the term of this patent is extended or adjusted under 35 U.S.C. 154(b) by 108 days.

(21) Appl. No.: 15/937,214

(22) Filed: Mar. 27, 2018

(65) Prior Publication Data
US 2018/0293427 A1 Oct. 11, 2018

(30) Foreign Application Priority Data
Mar. 28, 2017 (GB) .................................. 1704941.2

(51) Int. Cl.
*G06K 9/00* (2006.01)
*G06K 9/46* (2006.01)
*G01N 15/14* (2006.01)

(52) U.S. Cl.
CPC ..... *G06K 9/00147* (2013.01); *G01N 15/1475* (2013.01); *G06K 9/4642* (2013.01); *G01N 2015/1497* (2013.01)

(58) Field of Classification Search
CPC ........................................................ G06T 7/60
See application file for complete search history.

(56) References Cited

U.S. PATENT DOCUMENTS

| 5,978,497 A * | 11/1999 | Lee ................... G01N 15/1475 382/133 |
|---|---|---|
| 2005/0272073 A1 | 12/2005 | Vaisberg et al. |
| 2012/0114216 A1* | 5/2012 | Maddison ............ G06K 9/0014 382/133 |
| 2014/0030728 A1 | 1/2014 | Shioyama et al. |

(Continued)

FOREIGN PATENT DOCUMENTS

WO WO 2016/146469 9/2016

OTHER PUBLICATIONS

Loukas et al (NPL "An Image Analysis-Based Approach for Automated Counting of Cancer Cell Nuclei in Tissue Sections", p. 14, Cytometry Part A 55A:30-42). (Year: 2003).*

(Continued)

*Primary Examiner* — Oneal R Mistry
(74) *Attorney, Agent, or Firm* — Leason Ellis LLP

(57) ABSTRACT

A method of image classification is used for classifying images of stained cell nuclei. For each nucleus, the total integrated optical density is calculated and a histogram calculated. The image is then classified by automatically identifying peaks, identifying the lowest peak as a 2C peak and classifying the image as at least one of diploid, tetraploid, aneuploid or polyploid based on the number of peaks and the count at an integrated optical densities above the 2C peak.

7 Claims, 2 Drawing Sheets

(56) References Cited

U.S. PATENT DOCUMENTS

2018/0075598 A1* 3/2018 Kerr .................... G06K 9/0014

OTHER PUBLICATIONS

Agarwal Nitin et al., "DNA ploidy measure of Feulgen-stained cancer cells using three-dimensional image cytometry" 2014 IEEE Healthcare Innovation Conference (HIC); pp. 6-9; published Oct. 8, 2014, XP032734965.

Haroske G, Meyer W, Dimmer V, Kunze KD, Theissig F Zentralbl, "Feasibility and limitations of a cytometric DNA ploidy analysis procedure in tissue sections" Pathol.Feb. 1994, vol. 139, No. 6, pp. 407-417.

Wersto R P et al: "Flow cytometric DNA analysis of human solid tumors: A review of the interpretation of DNA histograms", Human Pathology. Saunders. Philadelphia. PA. us. vol. 22. No. 11. Nov. 1, 1991 (Nov. 1, 1991). pp. 1085-1098. XP026255636. ISSN: 0046-8177. DOI: 10.1016/0046-8177(91)90260-V [retrieved on Nov. 1, 1991] the whole document.

Heikki Joensuu et al: "Different opinions on classification of DNA histograms produced from paraffin-embedded tissue", Cytometry. vol. 10. No. 6. Oct. 18, 1989 (Oct. 18, 1989). pp. 711-717. XP055552070, us ISSN: 0196-4763, DOI: 10.1002jcyto.990100607 the whole document.

* cited by examiner

AUTOMATIC CALCULATION FOR PLOIDY CLASSIFICATION

CROSS-REFERENCE TO RELATED PATENT APPLICATIONS

The present application claims priority under 35 U.S.C. § 119 to British Patent Application No. 1704941.2, filed Mar. 28, 2017, which is hereby incorporated by reference in its entirety.

FIELD OF INVENTION

The present invention is concerned with a system for processing images of cell nuclei.

BACKGROUND TO THE INVENTION

The three main compartments of a cell are the nucleus, the cytoplasm and the membrane. The central nucleus is surrounded by the cytoplasm which is a gel-like fluid surrounded by the cell membrane.

In order to carry out DNA ploidy measurements, cells are processed to remove as far as possible the cytoplasm and membrane leaving only the nucleus. In practice, some cytoplasm remains. The processed cells may then be mounted on a slide for imaging.

DNA ploidy is a cytogenetic term for the number of single sets of chromosomes in a cell or organism. Diploid cells contain one pair of chromosomes, the normal state, and hence have a ploidy of 2. If the DNA duplicates without a subsequent cell division, the cell will contain two pairs of chromosomes and will be referred to as tetraploid.

Aneuploid cells contain a number of chromosomes that is not a multiple of the normal number, i.e. not a multiple of 2. In humans, aneuploid cells are abnormal and are a strong indication of malignancy.

Image cytometry may be used to measure the ploidy in human cells. The amount of DNA in a nucleus can be determined from the amount of light absorbed by the nuclei after a Feulgen stain is applied. The optical density, a measure of the transmittance of an optical element, may be measured on the Feulgen stained nuclei. DNA ploidy may be determined by calculating an integrated optical density, i.e. the sum of the optical density over a whole cell nucleus.

Image cytometry has the advantage of only measuring verifiable nuclei and hence results in limited or no cell debris being included in the analysis, which increases accuracy. In the past, human intervention has been used to identify cell nuclei. There is an increasing desire to automate this process, which increases the number of cell nuclei captured and measured, which in turn increases the ability to review the statistical significance of sub-populations. Increased automation also reduces the effect of subjective variations introduced by a human. Automation also allows for accurate grouping of cell types.

Challenges for automation of such a process include firstly locating, focussing and capturing data of cell nuclei. Secondly, there is a need to segment and calculate certain image characteristics as required for DNA ploidy classification. Thirdly, classification is required to identify intact nuclei and separate them from artefacts.

The greater the accuracy of such automatic methods and calculations the clearer aneuploid nuclei populations will be in comparison to normal diploid or tetraploid populations.

SUMMARY OF THE INVENTION

In accordance with a first aspect of the invention, there is provided a method of image classification according to claim 1.

The method uses the integrated optical density as a measure of the amount of DNA in the each nucleus. The 2C peak is identified and this, together with the count values at positions above the 2C peak, is used to automatically classify the image into one of diploid, tetraploid, polyploid or aneuploid.

The method gives good results automatically and without the need for human classification.

BRIEF DESCRIPTION OF THE DRAWINGS

An example of the invention will now be described with reference to the accompanying diagrams, in which.

Figure 1:
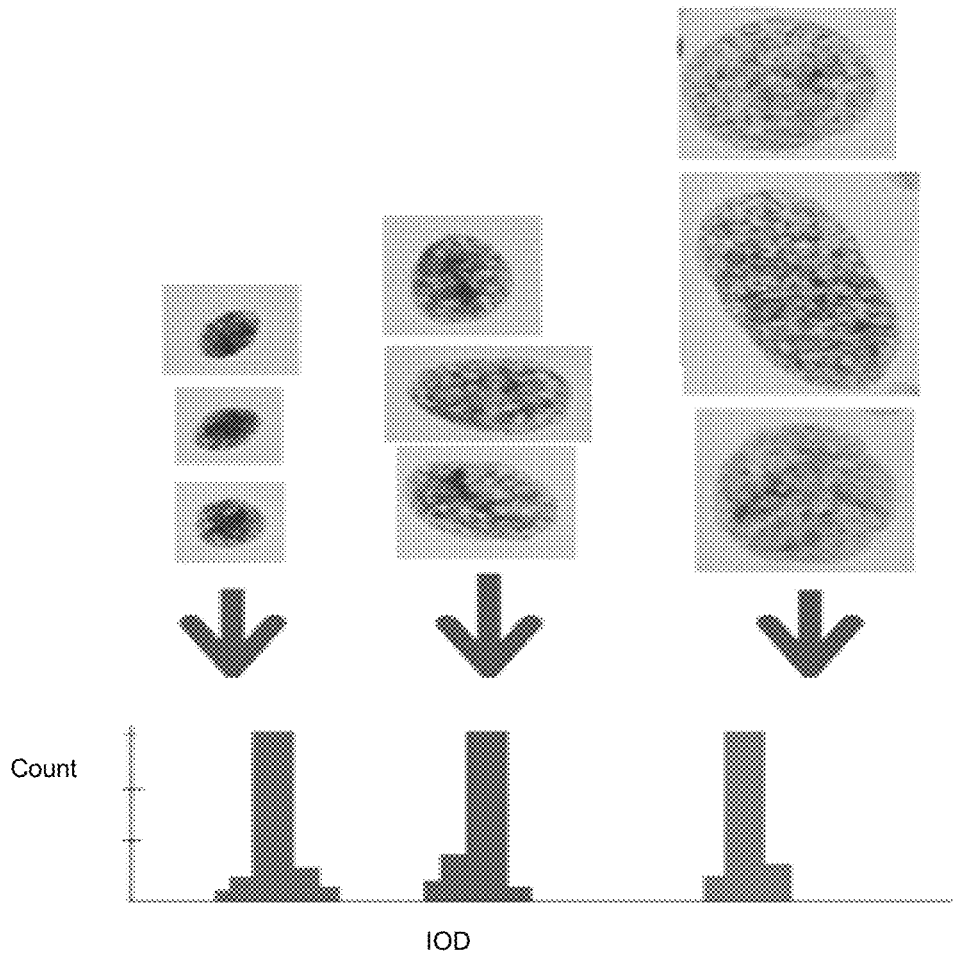
FIG. 1 illustrates an example histogram.

The Figures are schematic and not to scale.

DETAILED DESCRIPTION

An embodiment of the invention will now be described. Although the invention is specifically related to a method of classifying an image taken of a sample of tissue, the way in which that image is obtained will be described first.

Scanning

The method used to prepare the specimen prior to imaging is as follows. A block of paraffin embedded tissue is cut into sections and each section is mounted on a slide. To visualise the tissue, the slides a stained with Haematoxylin and Eosin and an image captured. This image will be referred to as the H & E image (Haemotoxylin and Eosin image). The area of the tumor was selected by a pathologist from the H&E image using a software tool (DLine).

The tumour area is microdissected from the paraffin block and cut into sections. A suspension of nuclei is obtained from the sections and put onto a slide in the form of a monolayer. The monolayer is stained with Feulgen's reagent ready for imaging.

Each object on the slide should be a nucleus. A Feulgen image of each object was scanned at high resolution. At the start of each scan an image of an area of the slide free from objects and artifacts was collected. This image is stored as the background image and is used to correct the frames for noise in the optics of the microscope.

Segmentation

The main image for each of a plurality of specimens was stored on a general purpose computer system which also contained software for carrying out the method as described below on the image.

For each object the following data were saved: Image of the object; Background for the object; shade corrected object; mask; and the shade corrected object with the mask applied.

Integrated Optical Density Calculation and Correction

The method calculates a parameter known as the integrated optical density for each relevant object.

Firstly all pixels in the object were corrected for glare and dark current. Then, shade correction was carried out using the object pixel value after glare and dark current correction and the background pixel value, again after glare and dark current correction, using the formula:

ShadeCorrectedPixelValue=ObjectPixelValue/BackgroundPixelValue*1023.0

Note that the number 1023 arises from the use of camera for detecting 10 bit data (0 to 1023).

The 2D integrated optical density was calculated using a method described in "Feasibility and limitations of a cytometric DNA ploidy analysis procedure in tissue sections" Haroske G, Meyer W, Dimmer V, Kunze K D, Theissig F Zentralbl Pathol. 1994 February, volume 139, number 6, pages 407-17. Instead of a "locally calculated mean value" described in that paper a constant 1023 was used.

The integrated optical density was calculated by adding the contributions to the integrated optical density from each pixel using the formula $$IOD = \sum -\log_{10} \frac{ShadeCorrectedPixelValue}{1023.0}$$

Thus, the method essentially adds a parameter for each pixel of the object, i.e. each pixel of the nucleus.

The integrated optical density is then corrected for background and other factors so the corrected integrated optical density can act as a measure of the amount of material stained by the Feulgen stain.

Histogram

A histogram is created and classified based on the corrected integrated optical density for the objects measured.

In more detail, the histogram is created based on a number of bins, i.e. groups of values of corrected integrated optical density, and each value of corrected IOD is assigned to one of the bins. The number of bins is set to 160 and maximum count is set to 16000.

FIG. 1 illustrates a histogram from a sample showing three peaks at different corrected integrated optical density values. Example nuclei corresponding each of the peaks are also illustrated.

The method identifies all of the peaks in the histogram are found, by first filtering the histogram by removing the bins where there are less than a threshold value of objects. The threshold is set to 1% of the total number of nuclei. For each candidate peak, the counts are used to determine the maximum count and the corrected integrated optical density of the peak.

The peak parameters of the peak are then determined to take account of the spread of the peak by starting at the centre of the peak and seeking a symmetric start and stop point from this point by going up and down the corrected integrated optical density values until the gradient (change in value between adjacent bins) becomes smaller than a predetermined value. To avoid this determining a small gradient at the edge of the plateau of a wide peak as the edge of the peak, if this small gradient occurs at a count value that is at least 90% of the peak value and there is a larger gradient further from the centre of the peak the method continues.

The peak parameters calculated are the start and stop bin position and the corresponding corrected IOD values; the total count in the peak; the CV for this peak; peak fraction; the number of bins in the peak and the mean corrected integrated optical density.

To determine if the peak is significant a test is completed using the total count in the peak and the max count of the biggest bin. For a peak to be significant the total count needs to be bigger than 3% of the count in the maximum peak and the peak count multiplied by 1.50 needs to be bigger than 6*(log 10(number of cells)−1/log 10(number of cells))+8.

When a peak is found the method then returns and identifies if there is another peak between this peak and the previous found peak. If there is a significant peak there, the missing peak is added to the list of peaks. If a missing peak is found, then a further check is carried out to identify if there is a further missing peak between the missing peak and the previous found peak—if there is this further missing peak is added as well.

Figure 2:
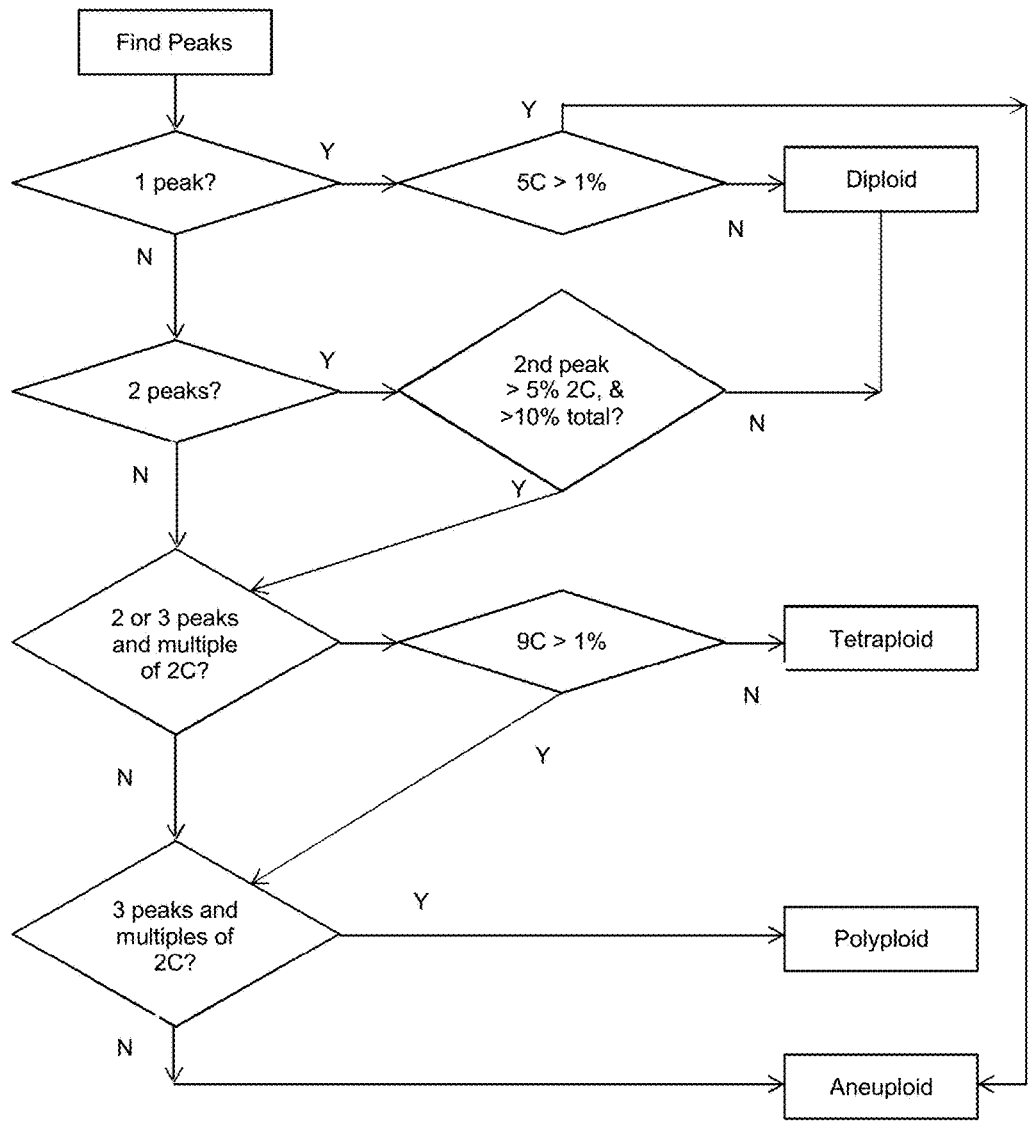
FIG. 2 illustrates a flow chart of a method according to an embodiment of the invention.

A classification method based on the peaks is then carried out based on the classification indicated in the flow chart of FIG. 2.

After generating the list of peaks, the peaks are checked to determine whether they are significant. The largest peak (with the maximum count in any bin) is identified and set as the 2C peak. A check is the carried out to identify completed to see if there is a small peak to the left of this, might be a non-diploid case with a small 2C population. This is completed by reviewing the list of peaks and if there is a significant peak to the left of the largest peak this is set to be the 2C peak instead of the largest peak.

If there is only one peak then the case is determined to be diploid, and the 5C fraction, 9C fraction and S phase fraction are calculated. The 5C and 9C fractions are the fraction of objects greater than the 5C position, i.e. the count of objects with a corrected integrated optical density greater than 2.5 times the corrected integrated optical density of the 2C position, and similarly the 9C fraction is the fraction of objects greater than the 9C position, with greater than 4.5 times the integrated optical density of the 2C position.

If there is more than one peak, then the S phase fraction is calculated for all peaks. The S-phase fraction is the fraction of nuclei in the S-phase, copying the cell DNA.

Further, a peak close to 2 times the 2C value is identified as G2/4C, i.e. as a 4C peak. A peak at close to 4 times the 2C value is identified as G2/8C, i.e. as an 8C peak. Other peaks are identified as aneuploid peaks and labelled A1, A2, A3 . . . . In the case of any aneuploid peaks the sample is classified as Aneuploid.

Then, if there is more than one peak, more than the lower limit of epithelial nuclei in gallery 1 (default 300,) and the number of cells in the first peak (2C) is bigger than the percentage set (default 1), then the decision tree in FIG. 2 is executed.

In particular, if there is either only one peak or alternatively two peaks with the second peak having an integrated count less than 5% of the 2C peak or the 5C fraction is less than the given limit default 10%, or 15% for prostate cases the image is classified as Diploid.

If there is at least one aneuploidy peak the image is classified as Aneuploid. If the image has only two peaks and the 9C exceeding rate is less than 1% the image is classified as Tetraploid or if there are more peaks with multiple of the 2C peak the image is classified as Polyploid.

It will be appreciated that the above classification can be modified if required. For example, there may be instances where it is appropriate to classify the samples into only two categories, diploid and non-diploid. In which case, the above method can be modified so that results are classified as diploid with a single peak and a 5C value less than or equal to 1%, or with two peaks, with the second peak not greater than 5% of the 2C value and not greater than 10% of the total value, and otherwise the sample would be classified as non-diploid.

It will also be appreciated that the values for the sizes of the peaks can all be varied as may be required by the skilled person in particular cases and for particular sample types. Accordingly, all of the values 1%, 5% and 10% described in the above method are not required and may if required be varied in the range half to double the above value—for example the test for a single peak being diploid need not require the 5C value to be less than or equal to 1%, but embodiments of the invention may use 0.5% or 2% or other values therebetween. Such values may be selected by the skilled person by varying the values in a computer algorithm and seeing what gives the best separation. Alternatively, algorithms for automatically determining appropriate classification boundaries exist and these may also be used.

The invention claimed is:

1. A method of image classification, comprising:
    receiving an image section of a plurality of cell nuclei;
    calculating a measure of the two-dimensional integrated optical density of a plurality of the nuclei;
    creating a histogram by counting the number of nuclei within each of a plurality of bins, each bin relating to a respective range of the measure of the two-dimensional integrated optical density; and
    classifying the image by:
    identifying the peaks of the histogram, their count and their integrated optical density;
    identifying the lowest peak as a 2C peak; and
    classifying the image as at least one of diploid, tetraploid, aneuploid or polyploid based on the number of peaks and the count at an integrated optical densities above the 2C peak.

2. The method according to claim 1, further comprising:
    if there is a single peak, calculating the total count at an integrated optical density at 2.5 times the integrated optical density at the peak of the 2C peak as a 5C-exceeding value, and classifying the image as diploid if the 5C-exceeding value is not greater than 1% and as aneuploid if the 5C-exceeding value is greater than 1%.

3. The method according to claim 1, further comprising:
    if there are two peaks, classifying the image as diploid If the peak that is not the lowest peak has a count of at least 5% of the number of the lowest peak but less than 10% of the total count.

4. The method according to claim 1
    wherein classifying the image further comprises:
    calculating the total count greater than 4.5× the integrated optical density corresponding to the 2c peak as a 9C-exceeding value;
    classifying the image as tetraploid if there are two or three peaks, and the 9C-exceeding value is less than 1% of the total count.

5. The method according to claim 4, further comprising:
    if the image is not classified as tetraploid, classifying the image as polyploid if there are three or more peaks at integral multiples of the integrated optical density of the 2C peak; and
    otherwise classifying the image as aneuploid.

6. A non-transitory computer readable medium for image classification of an image section of a plurality of cell nuclei, wherein the computer program product is arranged, when run on a computer, to cause the computer to carry out the steps of a method according claim 1.

7. An automatic classification system for an image section of a plurality of stained cell nuclei; comprising a computer and code for:
    calculating a measure of the two-dimensional integrated optical density of a plurality of the nuclei;
    creating a histogram by counting the number of nuclei within each of a plurality of bins, each bin relating to a respective range of the measure of the two-dimensional integrated optical density; and
    classifying the image by:
    identifying the peaks of the histogram, their count and their integrated optical density;
    identifying the lowest peak as a 2C peak; and
    classifying the image as at least one of diploid, tetraploid, aneuploid or polyploid based on the number of peaks and the count at an integrated optical densities above the 2C peak.

* * * * *